United States Patent
Chen et al.

(10) Patent No.: US 11,715,562 B2
(45) Date of Patent: Aug. 1, 2023

(54) METHOD FOR MULTI-CENTER EFFECT COMPENSATION BASED ON PET/CT INTELLIGENT DIAGNOSIS SYSTEM

(71) Applicants: ZHEJIANG LAB, Zhejiang (CN); MINFOUND MEDICAL SYSTEMS CO., LTD, Zhejiang (CN)

(72) Inventors: Ling Chen, Hangzhou (CN); Wentao Zhu, Hangzhou (CN); Bao Yang, Hangzhou (CN); Fan Rao, Hangzhou (CN); Hongwei Ye, Hangzhou (CN); Yaofa Wang, Hangzhou (CN)

(73) Assignees: ZHEJIANG LAB, Hangzhou (CN); MINFOUND MEDICAL SYSTEMS CO., LTD, Hangzhou (CN)

( * ) Notice: Subject to any disclaimer, the term of this patent is extended or adjusted under 35 U.S.C. 154(b) by 0 days.

(21) Appl. No.: 17/775,873

(22) PCT Filed: Jan. 23, 2021

(86) PCT No.: PCT/CN2021/073464
§ 371 (c)(1),
(2) Date: May 10, 2022

(87) PCT Pub. No.: WO2021/164495
PCT Pub. Date: Aug. 26, 2021

(65) Prior Publication Data
US 2022/0399119 A1    Dec. 15, 2022

(30) Foreign Application Priority Data
Feb. 21, 2020 (CN) .......................... 202010109082.9

(51) Int. Cl.
*G06V 10/77* (2022.01)
*G06V 10/84* (2022.01)
(Continued)

(52) U.S. Cl.
CPC .......... *G16H 50/20* (2018.01); *G06V 10/766* (2022.01); *G06V 10/774* (2022.01);
(Continued)

(58) Field of Classification Search
CPC .. G16H 50/20; G06V 10/766; G06V 10/7715; G06V 10/774; G06V 10/82;
(Continued)

(56) References Cited

U.S. PATENT DOCUMENTS

| | | | |
|---|---|---|---|
| 2005/0213844 A1 | 9/2005 | Min et al. | |
| 2016/0174902 A1* | 6/2016 | Georgescu | G06V 10/772 600/408 |

(Continued)

FOREIGN PATENT DOCUMENTS

| | | |
|---|---|---|
| CN | 101656883 A | 2/2010 |
| CN | 103954300 A | 7/2014 |

(Continued)

OTHER PUBLICATIONS

International Search Report (PCT/CN2021/073464); dated Apr. 27, 2021.
CN First Office Action(202010109082.9); dated Jan. 19, 2021.

*Primary Examiner* — Ming Y Hon
(74) *Attorney, Agent, or Firm* — W&G Law Group

(57) ABSTRACT

Disclosed is a method for multi-center effect compensation based on a PET/CT intelligent diagnosis system. The method includes the following steps: estimating multi-center effect parameters of a test center B relative to a training center A by implementing a nonparametric mathematical method for data of the training center A and the test center B based on a location-scale model about additive and multiplicative multi-center effect parameters, and using the parameters to compensate the data of the test center B to eliminate a multi-center effect between the test center B and
(Continued)

the training center A. According to the present disclosure, the multi-center effect between the training center A and the test center B can be compensated, so that the compensated data of the test center B can be used in the model trained by the training center A, and the generalization ability of the model is indirectly improved.

1 Claim, 2 Drawing Sheets

(51) Int. Cl.
*G06V 10/82* (2022.01)
*G06V 10/774* (2022.01)
*G16H 50/20* (2018.01)
*G06V 10/766* (2022.01)

(52) U.S. Cl.
CPC .......... *G06V 10/7715* (2022.01); *G06V 10/82* (2022.01); *G06V 10/84* (2022.01); *G06V 2201/03* (2022.01)

(58) Field of Classification Search
CPC .. G06V 10/84; G06V 2201/03; G06T 7/0012; A61B 6/032; A61B 6/037; A61B 6/5235; G06K 9/6232
See application file for complete search history.

(56) References Cited

U.S. PATENT DOCUMENTS

| 2018/0137657 | A1* | 5/2018 | Katsevich | G06T 5/002 |
| 2019/0050981 | A1* | 2/2019 | Song | A61B 5/7267 |
| 2020/0320685 | A1* | 10/2020 | Anssari Moin | G06T 11/005 |
| 2021/0174501 | A1* | 6/2021 | Takeshima | G06T 5/50 |
| 2021/0319210 | A1* | 10/2021 | Ichinose | G06K 9/6267 |
| 2021/0350935 | A1* | 11/2021 | Kinsey | G06F 30/23 |
| 2021/0401392 | A1* | 12/2021 | Bengtsson | A61B 6/5217 |
| 2021/0406596 | A1* | 12/2021 | Hoffman | G06K 9/6261 |
| 2022/0207791 | A1* | 6/2022 | Shi | G06N 3/088 |
| 2022/0327662 | A1* | 10/2022 | Matsuura | G06T 3/4053 |

FOREIGN PATENT DOCUMENTS

| CN | 107423760 A | 12/2017 |
| CN | 108022213 A | 5/2018 |
| CN | 111340768 A | 6/2020 |

* cited by examiner

METHOD FOR MULTI-CENTER EFFECT COMPENSATION BASED ON PET/CT INTELLIGENT DIAGNOSIS SYSTEM

CROSS-REFERENCE TO RELATED APPLICATIONS

The present application is a National Phase of International Application No. PCT/CN2021/073464, filed on Jan. 23, 2021, which claims priority to Chinese Application No. 202010109082.9, filed on Feb. 21, 2020, the contents of both of which are incorporated herein by reference in their entireties.

TECHNICAL FIELD

The present disclosure relates to the field of medical imaging and deep learning, in particular to a method for multi-center effect compensation based on a PET/CT intelligent diagnosis system.

BACKGROUND

Positron emission tomography (PET) is a functional imaging device at the molecular level. Before scanning, it is necessary to inject a radioactive tracer into a patient. The tracer decays in the patient's body and then annihilates, producing a pair of 511 keV gamma photons with opposite emission directions of about 180°. A detector will collect the position and time information of these gamma photons reaching the crystal. By using an image reconstruction algorithm to reconstruct and post-process the collected information, the metabolism and uptake of the radioactive tracer in the patient can be obtained. According to the image results of PET/CT and various clinical indicators, doctors comprehensively analyze the patient's condition, so as to determine a treatment plan.

A convolutional neural network (CNN) is one of the commonly used methods to build medical artificial intelligence models in recent years. It extracts high-order feature information of images through multi-layer convolution processing, and combines pool processing to reduce the dimension of features. The extracted high-order features are input to a subsequent specific network for specific tasks, such as classification, segmentation, registration, detection, noise reduction and so on. The advantage of this method is that it can automatically learn high-order features of significant significance for specific tasks through a large number of samples, but it has certain requirements for the amount of data used for training.

As for an existing intelligent diagnosis model, whether the model is based on single-center data or multi-center data training, the diagnostic efficiency of other center data that did not participate in the training will decrease for the center data that participate in the training. This is because different centers usually use different scanning protocols, which leads to different levels of image data in different centers. For example, on PET/CT, because different centers use different scanning times per bed, image reconstruction algorithms, iteration times/subset numbers, post-reconstruction filters, voxel sizes and other parameters, the PET/CT image data of these centers will have certain differences, that is, the above multi-center effect. This problem can be solved by fine tuning by adding the data that do not participate in the training center into the model, but this solution has certain requirements for the amount of data. However, the number of cases in grass-roots hospitals often falls far short of the sample size requirement for fine-tuning, so this method is not realistic for these grass-roots hospitals. Therefore, it is an important demand to solve the present disclosure problem of the multi-center intelligent diagnosis model in grass-roots hospitals.

SUMMARY

In view of the shortcomings of the prior art, the aim of the present disclosure is to provide a method for multi-center effect compensation based on a PET/CT intelligent diagnosis system. Using the location-scale model (L/S model) and the empirical Bayesian method, the feature maps of deep neural networks with different centers are standardized to eliminate the multi-center effect encountered in the application of an intelligent diagnosis model. Only the features of all data participating in model training need to be saved, and the features of data from a test center B are used for calculation, so that the multi-center effect parameters between the features of data from a training center A and the test center B can be estimated, and finally, the features of data from the test center B are compensated to the level of the features of data from the center A, and the compensated features of data from the test center B are applied to the intelligent diagnosis system of the training center A.

The purpose of the present disclosure is realized by the following technical solution: a method for multi-center effect compensation based on a PET/CT intelligent diagnosis system, specifically including the following steps:

Step 1, importing PET/CT data of a training center A into a deep convolution neural network model of the training center A, obtaining a feature map of all the PET/CT data in the training center A, calculating an average value $\hat{\alpha}_g$, a covariant regression coefficient $\hat{\beta}_g$ and a variance $\hat{\sigma}_g$ of all features $Y_{Ajg}$ in the feature map of all the PET/CT data in the training center A, and carrying out Z-Score standardization thereon to obtain a standardized feature $Z_{Ajg}$:

$$Z_{Ajg} = \frac{Y_{Ajg} - \hat{\alpha}_g - X\hat{\beta}_g}{\hat{\sigma}_g} \quad (1)$$

where $Z_{Ajg}$ represents a feature g extracted from a case j in the training center A, and X is a design matrix of a relevant covariates;

Step 2, importing PET/CT data in a test center B into the deep convolution neural network model of the training center A, obtaining a feature map of all the PET/CT data in the test center B, and carrying out Z-Score standardization on the features $Y_{Bjg}$ in the feature map by using the average value and the variance of the training center A obtained in step 1, and obtaining a standardized feature $Z_{Bjg}$:

$$Z_{Bjg} = \frac{Y_{Bjg} - \hat{\alpha}_g - X\hat{\beta}_g}{\hat{\sigma}_g}; \quad (2)$$

Step 3, estimating multi-center effect parameters $\gamma^*_{ig}$ and $\delta^*_{ig}$ according to the standardized features of the training center A and the test center B, and carrying out multi-center effect compensation for the feature of the test center B, so as to obtain a feature $Y^*_{ijg}$ of the test center B after the multi-center effect compensation, which comprise that following sub-steps:

(3.1) the standardized feature $Z_{Ajg}$ obtained in step 1 and the standardized feature $Z_{Bjg}$ obtained in step 2 conforming to a normal distribution, and calculating an average value $\hat{\gamma}_{ig}$ and a standard deviation $\hat{\delta}_{ig}^2$ of the standardized features; obtaining an expected value $E[\gamma_{ig}]$ about a multi-center effect parameter $\gamma_{ig}$ by integration from a posterior distribution $\pi(Z_{ig}, \gamma_{ig}, \delta_{ig}^2)$ of standardized data $Z_{ig}$; transforming the integral by a likelihood function according to the Bayesian theorem;

$$\hat{\gamma}_{ig} = \frac{1}{n_i} \sum_j Z_{ijg} \qquad (3)$$

$$\hat{\delta}_{ig}^2 = \frac{1}{n_{i-1}} \sum_j (Z_{ijg} - \hat{\gamma}_{ig})^2 \qquad (4)$$

$$E[\gamma_{ig}] = \int \gamma_{ig} \pi(Z_{ig}, \gamma_{ig}, \delta_{ig}^2) d(\gamma_{ig}, \delta_{ig}^2) \qquad (5)$$

$$E[\gamma_{ig}] = \frac{1}{C(Z_{ig})} \int \gamma_{ig} L(Z_{ig}|\gamma_{ig}, \delta_{ig}^2) \pi(\gamma_{ig}, \delta_{ig}^2) d(\gamma_{ig}, \delta_{ig}^2) \qquad (6)$$

where, $n_i$ represents a sample size of a center i; $Z_{19}$ represents the standardized features, in which i represents a center, j represents a case, and g represents a feature, $C(Z_{ig}) = \int L(Z_{ig}|\gamma_{ig}, \delta_{ig}^2) \pi(\gamma_{ig}, \delta_{ig}^2) d(\gamma_{ig}, \delta_{ig}^2)$ $L(Z_{ig}|\gamma_{ig}, \delta_{ig}^2) = \Pi_j \varphi(Z_{ijg}, \gamma_{ig}, \delta_{ig}^2)$, $\varphi(Z_{ijg}, \gamma_{ig}, \delta_{ig}^2)$ is a probability density function for evaluating a certain feature $Z_{ijg}$ about a random variable $N(\gamma_{ig}, \delta_{ig}^2)$ that conforms to the normal distribution;

(3.2) calculating an integral about the multi-center effect parameters by a Monte Carlo integral method, defining $w_{ig''} = L(Z_{ig}|\gamma_{ig''}, \delta_{ig''})$, so that an additive multi-center effect parameter $\gamma^*_{ig}$ can be estimated; using a same process to estimate a multiplicative multi-center effect $\delta^*_{ig}$:

$$\gamma^*_{ig} = \hat{E}(\gamma_{ig}) = \frac{\sum_{g''} w_{ig''} \hat{\gamma}_{ig''}^2}{\sum_{g''} w_{ig''}} \qquad (7)$$

$$\delta^*_{ig} = \hat{E}(\delta_{ig}) = \frac{\sum_{g''} w_{ig''} \hat{\delta}_{ig''}^2}{\sum_{g''} w_{ig''}} \qquad (8)$$

(3.3) substituting the multi-center effect parameters $\gamma^*_{Bg}$ and $\delta^*_{Bg}$ estimated in step (3.2) into the location-scale model to obtain the feature $Y^*_{Bjg}$ of the test center B after the multi-center effect compensation;

$$Y^*_{Bjg} = \frac{\hat{\sigma}_g}{\delta^*_{Bg}} (Z_{Bjg} - \hat{\gamma}^*_{Bg}) + \hat{\alpha}_g + X\hat{\beta}_g. \qquad (9)$$

The method has the beneficial effects that a location-scale model is used and the empirical Bayesian method is utilized to estimate the multi-center effect parameters, so as to eliminate the multi-center effect among different central data. For a test center B, the amount of data is not enough to fine-tune a deep convolution neural network model, which leads to the result that the model cannot achieve the desired effect in the center B. According to the present disclosure, the multi-center effect between the training center A and the test center B can be reduced, so that the standardized data of the test center B can be used in the model trained by the training center A, and the generalization ability of the model is indirectly improved. This method can indirectly improve the generalization ability of the intelligent diagnosis model, so that the intelligent diagnosis model trained in large-scale top-three hospitals can also be applied in grass-roots hospitals, which is very helpful for improving the diagnosis level of grass-roots hospitals and reducing the workload of doctors.

DESCRIPTION OF EMBODIMENTS

The present disclosure will be described in detail below with reference to the attached drawings.

Figure 1:
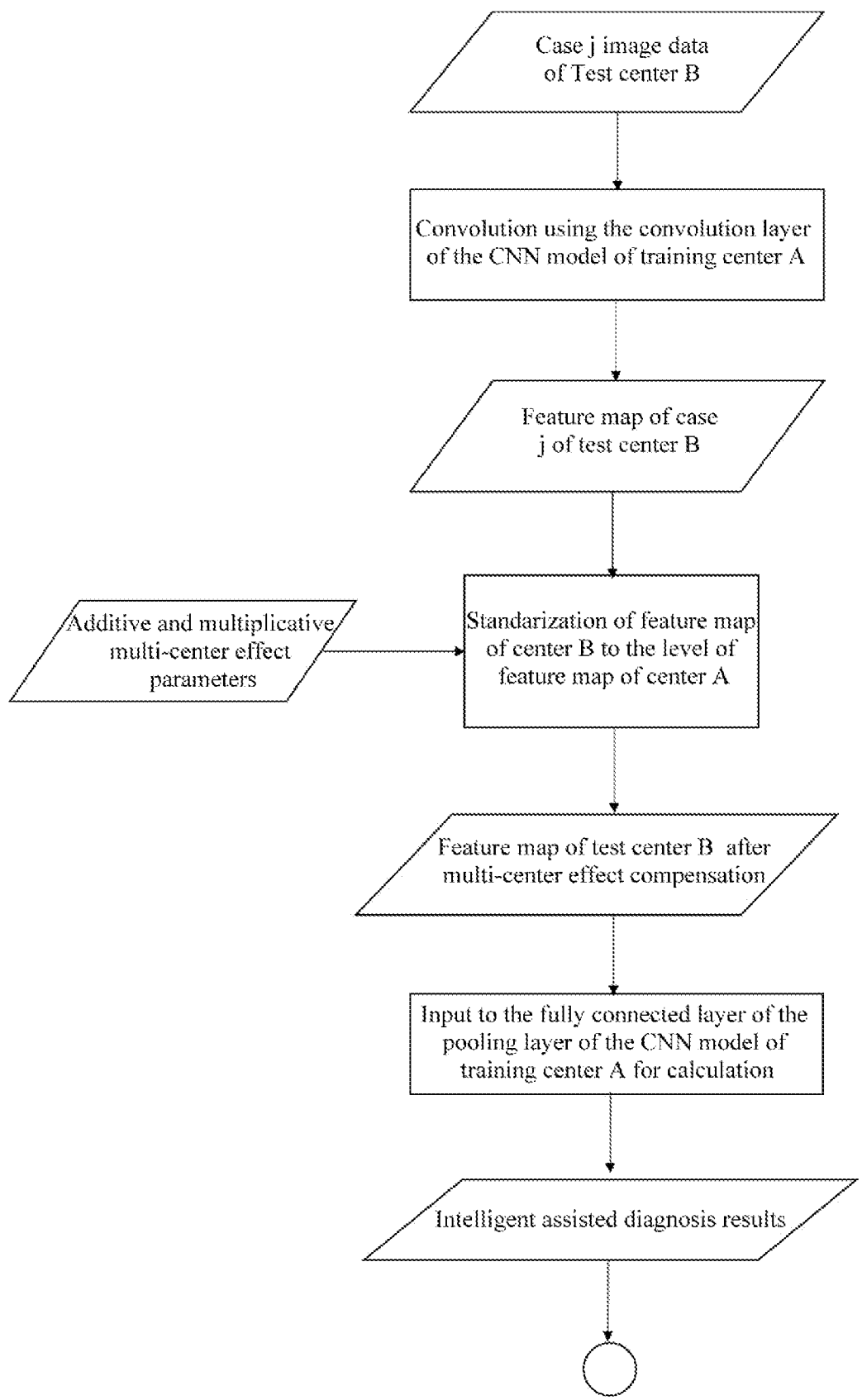
FIG. 1 is a flow chart of the multi-center compensation method of the present disclosure.
Figure 2:
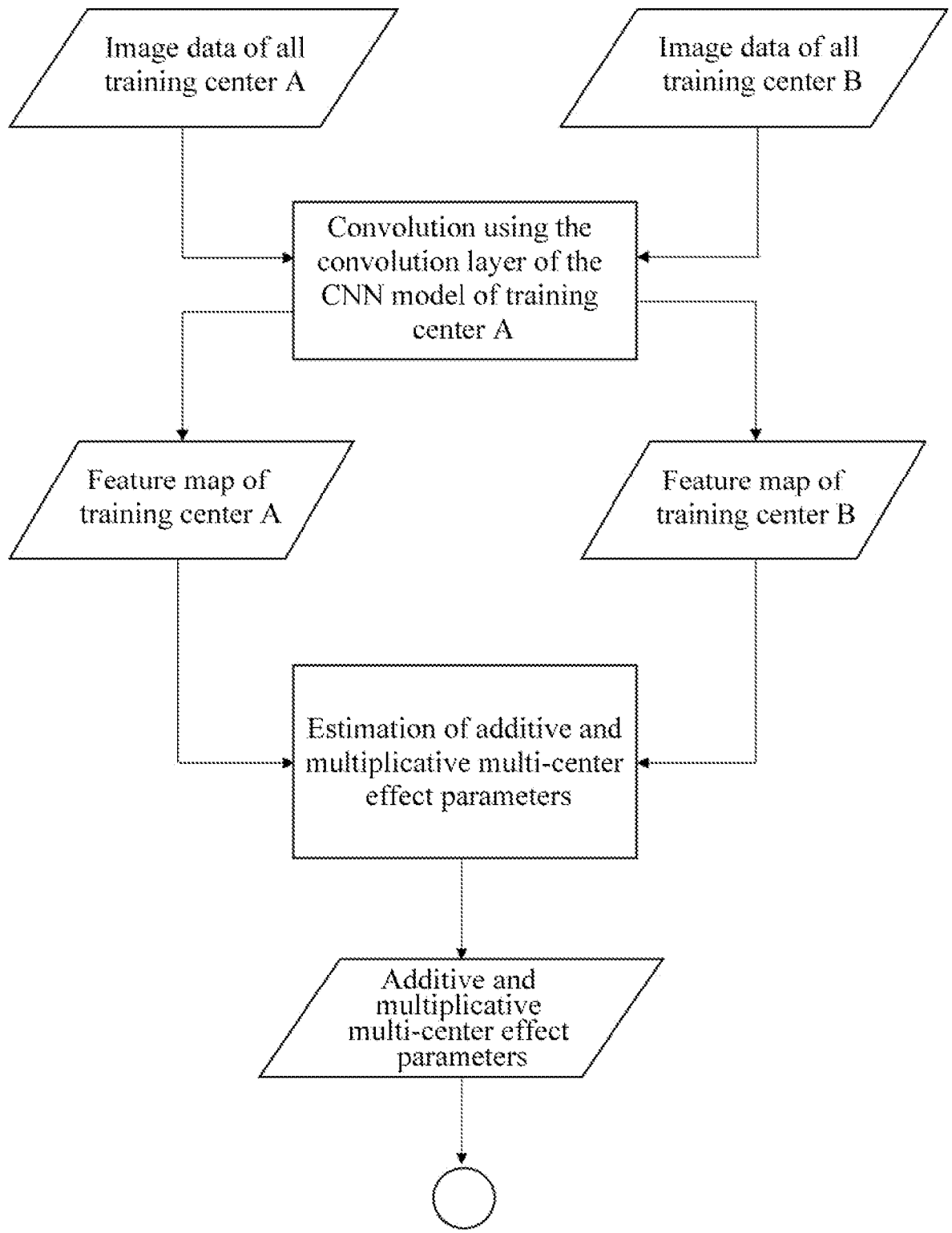
FIG. 2 is a flow chart showing the estimation of multi-center effect parameters.

FIG. 1 is a flow chart of a method for multi-center effect compensation based on a PET/CT intelligent diagnosis system of the present disclosure, which specifically includes the following steps:

Step 1, importing PET/CT data of a training center A into a deep convolution neural network model of the training center A, obtaining a feature map of all the PET/CT data in the training center A, calculating an average value $\hat{\alpha}_g$, a covariant regression coefficient $\hat{\beta}_g$ and a variance $\hat{\sigma}_g$ of all features $Y_{Ajg}$ in the feature map of all the PET/CT data in the training center A, and carrying out Z-Score standardization thereon to obtain a standardized feature $Z_{Ajg}$:

$$Z_{Ajg} = \frac{Y_{Ajg} - \hat{\alpha}_9 - X\hat{\beta}_g}{\hat{\sigma}_g} \qquad (1)$$

where $Z_{Ajg}$ represents a feature g extracted from a case j in the training center A, and X is a design matrix of a relevant covariates;

Step 2, importing PET/CT data in a test center B into the deep convolution neural network model of the training center A, obtaining a feature map of all the PET/CT data in the test center B, and carrying out Z-Score standardization on the features $Y_{Bjg}$ in the feature map by using the average value and the variance of the training center A obtained in step 1, and obtaining a standardized feature $Z_{Bjg}$:

$$Z_{Bjg} = \frac{Y_{Bjg} - \hat{\alpha}_g - X\hat{\beta}_g}{\hat{\sigma}_g}; \qquad (2)$$

Because the deep convolutional neural network model is trained based on the data of the training center A, the features of the test center B can be compensated to the level of the training center A through the above two steps.

Step 3, estimating multi-center effect parameters $\gamma^*_{ig}$ and $\delta^*_{ig}$ according to the standardized features of the training center A and the test center B, and carrying out multi-center effect compensation for the feature of the test center B, so as to obtain a feature $Y^*_{ijg}$ of the test center B after the multi-center effect compensation, which comprise that following sub-steps:

(3.1) the standardized feature $Z_{Ajg}$ obtained in step 1 and the standardized feature $Z_{Bjg}$ obtained in step 2 conforming to a normal distribution, and calculating an average value $\hat{\gamma}_{ig}$ and a standard deviation $\hat{\delta}_{ig}^2$ of the standardized features to be used as an observation value of the multi-center effect parameter; obtaining an expected value $E[\gamma_{ig}]$ about a multi-center effect parameter $\gamma_{ig}$ by integration from a posterior distribution $\pi(Z_{ig}, \gamma_{ig}, \delta_{ig}^2)$ of standardized data $Z_{ig}$ (formula 5); substituting the integral of formula 5 into the likelihood function to transform into formula 6 according to the Bayesian theorem, and obtaining an expected value of the calculation center parameter by the multi-center expected integral formula expressed by the likelihood function and prior probability.

$$\hat{\gamma}_{ig} = \frac{1}{n_i} \sum_j Z_{ijg} \quad (3)$$

$$\hat{\delta}_{ig}^2 = \frac{1}{n_i - 1} \sum_j (Z_{ijg} - \hat{\gamma}_{ig})^2 \quad (4)$$

$$E[\gamma_{ig}] = \int \gamma_{ig} \pi(Z_{ig}, \gamma_{ig}, \delta_{ig}^2) d(\gamma_{ig}, \delta_{ig}^2) \quad (5)$$

$$E[\gamma_{ig}] = \frac{1}{C(Z_{ig})} \int \gamma_{ig} L(Z_{ig}|\gamma_{ig}, \delta_{ig}^2) \pi(\gamma_{ig}, \delta_{ig}^2) d(\gamma_{ig}, \delta_{ig}^2) \quad (6)$$

where, $n_i$ represents a sample size of a center i; $Z_{ijg}$ represents the standardized features, in which i represents a center, j represents a case, and g represents a feature, $C(Z_{ig}) = \int L(Z_{ig}|\gamma_{ig}, \delta_{ig}^2) \pi(\gamma_{ig}, \delta_{ig}^2) d(\gamma_{ig}, \delta_{ig}^2)$ $L(Z_{ig}|\gamma_{ig}, \delta_{ig}^2) = \Pi_j \varphi(Z_{ig}, \gamma_{ig}, \delta_{ig}^2)$, $\varphi(Z_{ig}, \gamma_{ig}, \delta_{ig}^2)$ is a probability density function for evaluating a certain feature $Z_{ijg}$ about a random variable $N(\gamma_{ig}, \delta_{ig}^2)$ that conforms to the normal distribution;

(3.2) calculating the multi-center effect parameter integral of formula 6 by a Monte Carlo integration method, defining $w_{ig'} = L(Z_{ig}|\hat{\gamma}_{ig'}, \hat{\delta}_{ig'})$, so that an additive multi-center effect parameter $\gamma_{ig}^*$, can be estimated; using a same process to estimate a multiplicative multi-center effect $\delta_{ig}^*$; a numerical integration method-Monte Carlo integration is used to estimate the integration result of formula 6, which avoids using an analytical method to calculate the integration.

$$\gamma_{ig}^* = \hat{E}(\gamma_{ig}) = \frac{\sum_{g''} w_{ig''} \hat{\gamma}_{ig''}^2}{\sum_{g''} w_{ig''}} \quad (7)$$

$$\delta_{ig}^* = \hat{E}(\delta_{ig}) = \frac{\sum_{g''} w_{ig''} \hat{\delta}_{ig''}^2}{\sum_{g''} w_{ig''}} \quad (8)$$

(3.3) substituting the multi-center effect parameters $\gamma^*_{Bg}$ and $\delta^*_{Bg}$ estimated in step (3.2) into the location-scale model to obtain the feature $Y^*_{Bjg}$ of the test center B after the multi-center effect compensation;

$$Y^*_{Bjg} = \frac{\hat{\sigma}_g}{\hat{\delta}^*_{Bg}} (Z_{Bjg} - \hat{\gamma}^*_{Bg}) + \hat{\alpha}_g + X\hat{\beta}_g. \quad (9)$$

Examples

Taking the deep convolution neural network ResNet-152 as an example, how to apply this method for multi-center effect compensation to the deep convolution neural network will be explained.

The network structure of ResNet-152 is shown in Table 1:

TABLE 1

| Resnet-152 Network Structure | |
|---|---|
| Layer name | Detail |
| Convolution layer 1 | 7 * 7, stride 2 |
| Convolution layer 2 | 3 * 3 max pool, stride 2 |
| | $\begin{bmatrix} 1*1, & 64 \\ 3*3, & 64 \\ 1*1, & 256 \end{bmatrix} *3$ |
| Convolution layer 3 | $\begin{bmatrix} 1*1, & 128 \\ 3*3, & 128 \\ 1*1, & 512 \end{bmatrix} *8$ |
| Convolution layer 4 | $\begin{bmatrix} 1*1, & 256 \\ 3*3, & 256 \\ 1*1, & 1024 \end{bmatrix} *36$ |
| Convolution layer 5 | $\begin{bmatrix} 1*1, & 512 \\ 3*3, & 512 \\ 1*1, & 2048 \end{bmatrix} *3$ |
| Mean value pooling layer + 1000-dimensional fully connected layer + softmax | |

In an actual implementation process, a training center A used the PET/CT image data of this center to train an intelligent auxiliary diagnosis model of benign and malignant tumors based on ResNet-152. Now, this intelligent auxiliary diagnosis model was used in a test center B, a grass-roots hospital. However, due to the statistical differences between the imaging protocols used by the training center A and the test center B, if the model was directly used in the test center B, the diagnostic efficiency would be reduced to some extent. Therefore, the above problems were solved by the method for multi-center effect compensation of the present disclosure. The implementation steps were as follows:

(1) All the image data used for training in the training center A were input into ResNet-152 after training, and a feature map of the last layer of a convolution layer 5 was extracted and saved as features.

(2) All available image data of THE test center B were input into the trained ResNet-152, and the feature map of the last layer of the convolution layer 5 was extracted and saved as features.

(3) Based on the features of the two groups obtained in step (1) and step (2), the additive and multiplicative multi-center effect parameters were estimated by using the method for multi-center effect compensation proposed by the present disclosure.

(4) By using the multi-center effect parameters obtained in step (3), the features of the test center B were compensated for a multi-center effect.

(5) The compensated features of the test center B were returned to the second half of ResNet-152, that is, the mean value pooling layer behind the convolution layer 5, the 1000-dimensional fully connected layer and the softmax layer, so as to obtain the classification results of benign and malignant tumors.

After the estimated parameters of multi-center effect were saved, the steps (1) and (3) could be omitted in the subsequent diagnosis application as follow:

(1) The image data to be tested in the test center B were input into the diagnosis model ResNet-152, and the feature map of the last layer of the convolution layer 5 was extracted as features.

(2) By using the obtained additive and multiplicative multi-center effect parameters, the features obtained in step (1) were compensated for a multi-center effect.

(3) The compensated features of test center B were returned to the second half of ResNet-152, that is, the mean value pooling layer behind convolution layer 5, the 1000-dimensional fully connected layer and the softmax layer, so as to obtain the classification results of benign and malignant tumors.

Due to the multi-center effect compensation, the data of the test center B is applied to the diagnosis model of the training center A, which has a similar diagnosis efficiency to that of the training center A, and indirectly improves the generalization ability of the model.

It should be noted that when the data compression apparatus provided in the foregoing embodiment performs data compression, division into the foregoing functional modules is used only as an example for description. In an actual application, the foregoing functions can be allocated to and implemented by different functional modules based on a requirement, that is, an inner structure of the apparatus is divided into different functional modules, to implement all or some of the functions described above. For details about a specific implementation process, refer to the method embodiment. Details are not described herein again.

All or some of the foregoing embodiments may be implemented by using software, hardware, firmware, or any combination thereof. When the software is used for implementation, all or some of the embodiments may be implemented in a form of a computer program product. The computer program product includes one or more computer instructions. When the computer program instructions are loaded and executed on a server or a terminal, all or some of the procedures or functions according to the embodiments of this application are generated. The computer instructions may be stored in a computer-readable storage medium or may be transmitted from a computer-readable storage medium to another computer-readable storage medium. For example, the computer instructions may be transmitted from a web site, computer, server, or data center to another web site, computer, server, or data center in a wired (for example, a coaxial optical cable, an optical fiber, or a digital subscriber line) or wireless (for example, infrared, radio, or microwave) manner. The computer-readable storage medium may be any usable medium accessible by a server or a terminal, or a data storage device, such as a server or a data center, integrating one or more usable media. The usable medium may be a magnetic medium (for example, a floppy disk, a hard disk, or a magnetic tape), an optical medium (for example, a digital video disk (DVD)), or a semiconductor medium (for example, a solid-state drive).

The steps of the method or algorithm described combined with the embodiments of the present disclosure may be implemented in a hardware manner, or may be implemented in a manner in which a processor executes software instructions. The software instructions may consist of corresponding software modules, and the software modules can be stored in Random Access Memory (RAM), flash memory, Read Only Memory (ROM), Erasable Programmable ROM (EPROM), Electrically Erasable Programmable Read-Only Memory (EEPROM), registers, hard disks, removable hard disks, CD-ROMs or any other forms of storage media well-known in the art. An exemplary storage medium is coupled to the processor, such that the processor can read information from, and write information to, the storage medium. The storage medium can also be an integral part of the processor. The processor and storage medium may reside in an Application Specific Integrated Circuit (ASIC). Alternatively, the ASIC may be located in a node device, such as the processing node described above. In addition, the processor and storage medium may also exist in the node device as discrete components.

What is claimed is:

1. A method for multi-center effect compensation based on a PET/CT intelligent diagnosis system, comprising the following steps:

importing PET/CT data of a training center A into a deep convolution neural network model of the training center A, obtaining a feature map of all the PET/CT data in the training center A, calculating an average value $\hat{\alpha}_g$, a covariant regression coefficient $\hat{\beta}_g$ and a variance $\hat{\sigma}_g$ of all features $Y_{Ajg}$ in the feature map of all the PET/CT data in the training center A, and carrying out Z-Score standardization thereon to obtain a standardized feature $Z_{Ajg}$:

$$Z_{Ajg} = \frac{Y_{Ajg} - \hat{\alpha}_9 - X\hat{\beta}_g}{\hat{\sigma}_g} \quad (1)$$

where $Z_{Ajg}$ represents a feature g extracted from a case j in the training center A, and X is a design matrix of a relevant covariates;

importing PET/CT data in a test center B into the deep convolution neural network model of the training center A, obtaining a feature map of all the PET/CT data in the test center B, and carrying out Z-Score standardization on the features $Y_{Bjg}$ in the feature map by using the average value and the variance of the training center A, and obtaining a standardized feature $Z_{Bjg}$:

$$Z_{Bjg} = \frac{Y_{Bjg} - \hat{\alpha}_g - X\hat{\beta}_g}{\hat{\sigma}_g}; \quad (2)$$

estimating multi-center effect parameters $\gamma^*_{ig}$, and $\delta^*_{ig}$, according to the standardized features of the training center A and the test center B, and carrying out multi-center effect compensation for the feature of the test center B, so as to obtain a feature $Y^*_{ijg}$ of the test center B after the multi-center effect compensation, which comprise following sub-steps:

the standardized feature $Z_{Ajg}$ and the standardized feature $Z_{Bjg}$ conforming to a normal distribution, and calculating an average value $\hat{\gamma}_{ig}$ and a standard deviation $\hat{\delta}_{ig}^2$ of the standardized features; obtaining an expected value $E[\gamma_{ig}]$ about a multi-center effect parameter $\gamma_{ig}$ by integration from a posterior distribution $\pi(Z_{ig}, \gamma_{ig}, \delta_{ig}^2)$ of standardized data $Z_{ig}$; transforming the integral by a likelihood function according to the Bayesian theorem;

$$\hat{\gamma}_{ig} = \frac{1}{n_i}\sum_j Z_{ijg} \quad (3)$$

$$\hat{\delta}_{ig}^2 = \frac{1}{n_{i-1}}\sum_j (Z_{ijg} - \hat{\gamma}_{ig})^2 \quad (4)$$

$$E[\gamma_{ig}] = \int \gamma_{ig}\pi(Z_{ig}, \gamma_{ig}, \delta_{ig}^2)d(\gamma_{ig}, \delta_{ig}^2) \quad (5)$$

$$E[\gamma_{ig}] = \frac{1}{C(Z_{ig})} \int \gamma_{ig} L(Z_{ig}|\gamma_{ig}, \delta_{ig}^2) \pi(\gamma_{ig}, \delta_{ig}^2) d(\gamma_{ig}, \delta_{ig}^2) \quad (6)$$

where $n_i$ represents a sample size of a center i; $Z_{ijg}$ represents the standardized features, in which i represents a center, j represents a case, and g represents a feature, $C(Z_{ig}) = \int L(Z_{ig}|\gamma_{ig}, \delta_{ig}^2) \pi(\gamma_{ig}, \delta_{ig}^2) d(\gamma_{ig}, \delta_{ig}^2)$, $L(Z_{ig}|\gamma_{ig}, \delta_{ig}^2) = \Pi_j \varphi(Z_{ijg}, \gamma_{ig}, \delta_{ig}^2)$, $\varphi(Z_{ijg}, \gamma_{ig}, \delta_{ig}^2)$ is a probability density function for evaluating a certain feature $Z_{ijg}$ about a random variable $N(\gamma_{ig}, \delta_{ig}^2)$ that conforms to the normal distribution;

calculating an integral about the multi-center effect parameters by a Monte Carlo integral method, defining $w_{ig''} = L(Z_{ig}|\hat{\gamma}_{ig''}, \hat{\delta}_{ig''})$, so that an additive multi-center effect parameter $\gamma^*_{ig}$ can be estimated; using a same process to estimate a multiplicative multi-center effect $\delta^*_{ig}$;

$$\gamma^*_{ig} = \hat{E}(\gamma_{ig}) = \frac{\sum_{g''} w_{ig''} \hat{\gamma}^2_{ig''}}{\sum_{g''} w_{ig''}} \quad (7)$$

$$\delta^*_{ig} = \hat{E}(\delta_{ig}) = \frac{\sum_{g''} w_{ig''} \hat{\delta}^2_{ig''}}{\sum_{g''} w_{ig''}} \quad (8)$$

substituting the multi-center effect parameters $\gamma^*_{Bg}$ and $\delta^*_{Bg}$ into the location-scale model to obtain the feature $Y^*_{Bjg}$ of the test center B after the multi-center effect compensation;

$$Y^*_{Bjg} = \frac{\hat{\sigma}_g}{\hat{\delta}^*_{Bg}}(Z_{Bjg} - \hat{\gamma}^*_{Bg}) + \hat{\alpha}_g + X\hat{\beta}_g. \quad (9)$$

* * * * *